(12) United States Patent
Priemer

(10) Patent No.: US 7,351,207 B2
(45) Date of Patent: Apr. 1, 2008

(54) EXTRACTION OF ONE OR MORE DISCRETE HEART SOUNDS FROM HEART SOUND INFORMATION

(75) Inventor: Roland Priemer, Des Plaines, IL (US)

(73) Assignee: The Board of Trustees of The University of Illinois, Urbana, IL (US)

( * ) Notice: Subject to any disclaimer, the term of this patent is extended or adjusted under 35 U.S.C. 154(b) by 365 days.

(21) Appl. No.: 10/893,627

(22) Filed: Jul. 16, 2004

(65) Prior Publication Data

US 2005/0043643 A1 Feb. 24, 2005

Related U.S. Application Data

(60) Provisional application No. 60/537,941, filed on Jan. 21, 2004, provisional application No. 60/488,311, filed on Jul. 18, 2003.

(51) Int. Cl.
*A61B 5/02* (2006.01)
(52) U.S. Cl. .................................................. 600/528
(58) Field of Classification Search ................. 600/528
See application file for complete search history.

(56) References Cited

U.S. PATENT DOCUMENTS

| | | | |
|---|---|---|---|
| 4,304,240 A | 12/1981 | Perlin | |
| 5,012,815 A | 5/1991 | Bennett, Jr. et al. | |
| 6,236,862 B1 * | 5/2001 | Erten et al. | 455/501 |
| 6,544,189 B2 | 4/2003 | Watrous | |
| 6,572,560 B1 | 6/2003 | Watrous et al. | |
| 6,629,937 B2 | 10/2003 | Watrous | |
| 6,878,117 B1 | 4/2005 | Watrous | |
| 6,953,436 B2 | 10/2005 | Watrous et al. | |
| 6,993,378 B2 * | 1/2006 | Wiederhold et al. | 600/509 |
| 7,022,077 B2 * | 4/2006 | Mourad et al. | 600/449 |
| 7,096,060 B2 | 8/2006 | Arand et al. | |
| 2003/0018276 A1 * | 1/2003 | Mansy et al. | 600/529 |
| 2003/0229289 A1 * | 12/2003 | Mohler et al. | 600/508 |
| 2004/0260188 A1 * | 12/2004 | Syed et al. | 600/509 |

OTHER PUBLICATIONS

Xuesong Ye et al, "The Research of Diagnosis of Coronary Artery Disease Based on the Application of Independent Component Analysis to Heart Sounds Sensory Array", Chinese Journal of Sensors and Actuators, Southeast University China, vol. 16, No. 1, 2003, pp. 16-20, China.

Vigon, L. et al, "Quantitative Evaluation of Techniques for Ocular Artefact Filtering Of EEG Waveforms", IEE Proceedings-Science, Measurement and Technology IEE UK, vol. 147, No. 5, Sep. 2000, pp. 219-228, United Kingdom.

Mustafa H. et al., "Phococardiography nonlinear multiple measurements in discovering the abnormalities in the bioprosthetic heart valves", Proceedings of SPIE—The International Society for Optical Engineering, vol. 4391, 2001, pp. 465-479, USA.

Krishna G. Ramachandran; Cardiac Sound Separation; Sep. 2002; 227 pgs.; Chicago, Illinois.

* cited by examiner

*Primary Examiner*—George Manuel
*Assistant Examiner*—Christopher A. Flory
(74) *Attorney, Agent, or Firm*—Wood, Phillips, Katz, Clark & Mortimer; Robert J. Brill

(57) ABSTRACT

A heart sound analyzer component of an apparatus in one example extracts from composite heart sound information one or more discrete heart sounds of one or more corresponding distinct heart sound sources.

19 Claims, 11 Drawing Sheets

Stethoscopic heart sound analyzer

Stethoscopic heart sound analyzer

Block diagram of stethoscopic heart sound analyzer

Source separation procedure

Heart model

Timing diagram of valve operation

A sample heart sound (approx. 1 sec. duration) depicted with:
    S4, a low frequency sound preceding S1,
    S1, the first heart sound, due mainly to M1 and T1,
    S2, the second heart sound, due mainly to A2 and P2,
    S3, a low frequency sound following A2 and P2, and background noise Separated sounds (approx. 1 sec. duration) from top to bottom: S3, pulmonary, background noise, aortic, tricuspid, S4, mitral Abnormal heart sound with a VSD murmur Separated heart sounds showing the VSD murmur and the other sounds Alternate front end of stethoscopic heart sound analyzer Esophageal sensor pod

EXTRACTION OF ONE OR MORE DISCRETE HEART SOUNDS FROM HEART SOUND INFORMATION

CROSS-REFERENCE TO RELATED APPLICATIONS

This application claims the priority of U.S. provisional Patent Application Ser. No. 60/488,311 (by Roland Priemer, filed Jul. 18, 2003, and entitled "CARDIAC SOUND SEPARATOR AND STETHOSCOPE").

This application claims the priority of U.S. provisional Patent Application Ser. No. 60/537,941 (by Roland Priemer, filed Jan. 21, 2004, and entitled "EXTRACTION OF ONE OR MORE DISCRETE HEART SOUNDS FROM HEART SOUND INFORMATION").

This application contains subject matter that is related to the subject matter of the following applications, which are assigned to the same assignee as this application. The below-listed applications are hereby incorporated herein by reference in their entireties.

U.S. Application No. 10/892,748 (by Priemer, et al., filed Jul. 16, 2004, entitled "EXTRACTION OF HEART SOUND OF FETUS FROM HEART SOUND INFORMATION THAT COMPRISES PLURALITY OF MIXTURES OF PLURALITY OF HEART SOUNDS OF PLURALITY OF FETUSES").

International Application No. PCT/US 04/23049 (by Roland Priemer, filed Jul. 16, 2004, entitled "IDENTIFICATION OF ONE OR MORE DISTINCT HEART SOUND SOURCES THAT PRODUCE ONE OR MORE DISCRETE HEART SOUNDS").

International Application No. PCT/US 04/22738 (by Priemer, et al., filed Jul. 16, 2004, entitled "HEART SOUND ANALYZER COMPONENT THAT EXTRACTS HEART SOUND OF FETUS FROM HEART SOUND INFORMATION THAT COMPRISES PLURALITY OF MIXTURES OF PLURALITY OF HEART SOUNDS OF PLURALITY OF FETUSES").

TECHNICAL FIELD

This invention relates generally to the medical arts and more particularly to sensing of heart sound information.

BACKGROUND

Doctors examine heart sounds of a patient's heart to diagnose heart dysfunctions. Among other sources, the opening and closing of the heart valves cause the heart sounds. The human heart sounds comprise a first major sound ("S1"), a second major sound ("S2"), a noise sound component, low frequency sounds, and/or an abnormal sound. For example, the first major sound comprises a mitral valve sound and a tricuspid valve sound. Further, the second major sound comprises an aortic valve sound and a pulmonary valve sound.

In some examinations, doctors employ acoustic stethoscopes to listen to the heart sounds, for example, acoustic heart sounds. To learn how to use the acoustic stethoscopes, doctors undergo extensive training. As one shortcoming, doctors require extensive training with acoustic stethoscopes to diagnose heart dysfunctions. As another shortcoming, acoustic stethoscopes allow doctors to discern only between the first major sound and the second major sound. For example, acoustic stethoscopes cannot detect individual valve dysfunctions.

In other examinations, doctors employ electronic stethoscopes to listen to the heart sounds. The electronic stethoscopes convert the acoustic heart sounds into electrical heart sounds. Upon conversion to the electrical heart sounds, the electronic stethoscopes can filter and amplify the electrical heart sounds. For example, the electronic stethoscopes output frequency and amplitude modified heart sound information. To diagnose general heart dysfunctions, a doctor can employ the electronic stethoscope to listen to the frequency and amplitude modified heart sound information. However, the electronic stethoscope cannot identify a source of a heart dysfunction. As one shortcoming, the doctors are unable to diagnose the sources of heart dysfunctions with the electronic stethoscope. For example, the electronic stethoscope cannot separate the composite heart sound into sounds from discrete sources of the heart.

Thus, a need exists for a capability to identify one or more sources of one or more heart functions and/or dysfunctions.

SUMMARY

The invention in one implementation encompasses an apparatus. The apparatus comprises a heart sound analyzer component that extracts from composite heart sound information one or more discrete heart sounds of one or more corresponding distinct heart sound sources.

Another implementation of the invention encompasses an apparatus. The apparatus comprises a plurality of microphones of a stethoscope sensor head that are employable to capture a plurality of composite heart sounds that allow extraction of one or more discrete heart sounds from the plurality of composite heart sounds.

Yet another implementation of the invention encompasses a method. Composite heart sound information is obtained from a heart. One or more discrete heart sounds of one or more corresponding distinct heart sound sources are extracted from the composite heart sound information.

DESCRIPTION OF THE DRAWINGS

Features of exemplary implementations of the invention will become apparent from the description, the claims, and the accompanying drawings in which:

DETAILED DESCRIPTION

Figure 1:
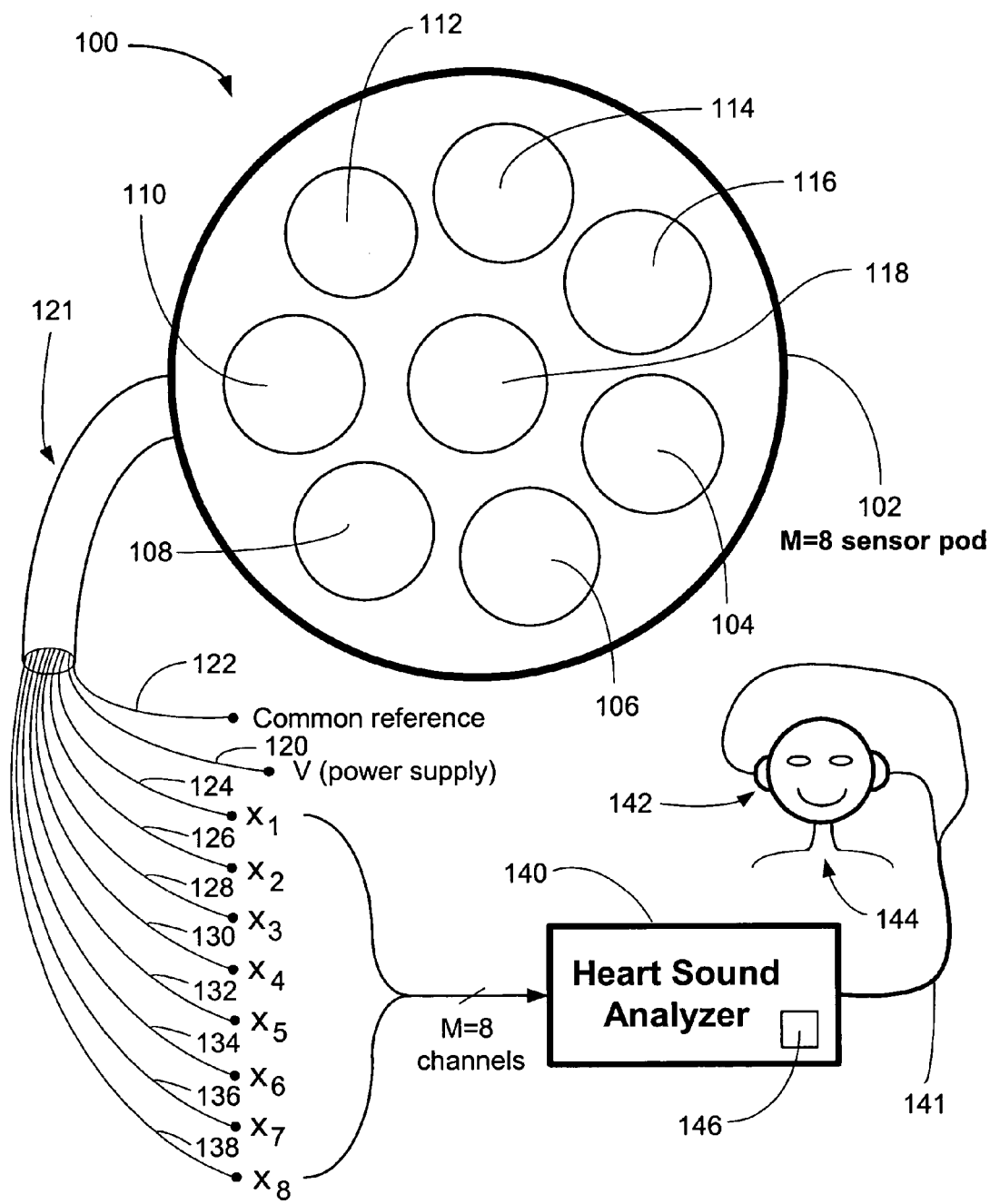
FIG. 1 is a representation of one exemplary implementation of an apparatus that comprises a sensor array, one or more sensors, one or more signal paths, a heart sound analyzer, and one or more speaker components.

Turning to FIG. 1, an apparatus 100 in one example comprises a sensor array 102, a plurality, for example, eight, of sensors 104, 106, 108, 110, 112, 114, 116, and 118, one or more signal paths 120, 122, 124, 126, 128, 130, 132, 134, 136, and 138, a heart sound analyzer 140, and one or more speaker components 142. The sensor array 102 in one example obtains heart sound information 121 from a human heart. For example, the sensors 104, 106, 108, 110, 112, 114, 116, and 118 capture the heart sound information 121 from the human heart. The heart sound information 121 is a plurality of composite heart sounds, where each composite heart sound is a mixture of a plurality of discrete heart sounds from a plurality of corresponding distinct heart sound sources. The sensors 104, 106, 108, 110, 112, 114, 116, and 118 pass the heart sound information 121 through the signal paths 124, 126, 128, 130, 132, 134, 136, and 138 to the heart sound analyzer 140. The heart sound analyzer 140 extracts from the heart sound information 121 one or more discrete heart sounds of the corresponding distinct heart sound sources. The heart sound analyzer 140 in one example comprises a stethoscopic heart sound analyzer.

Referring to FIGS. 1 and 4-9, blood flows through one or more chambers and one or more valves of the human heart to produce the heart sound information 121 provided to the heart sound analyzer 140. The normal human heart comprises a left atrium 402, a right atrium 404, a mitral valve 406, a tricuspid valve 408, a right ventricle 410, a left ventricle 412, an aortic valve 414, and a pulmonary valve 418.

Oxygenated blood flows into the left atrium 402 from one or more pulmonary veins. The left atrium 402 pumps the oxygenated blood through the mitral valve 406 into the left ventricle 412. The left ventricle 412 pumps the oxygenated blood through the aortic valve 414 into the aorta 416.

Deoxygenated blood flows into the right atrium 404 from a superior vena cava and an inferior vena cava. The right atrium 404 pumps the deoxygenated blood through the tricuspid valve 408 into the right ventricle 410. The right ventricle 410 pumps the deoxygenated blood through the pulmonary valve 418 into the pulmonary artery 420.

Figure 5:
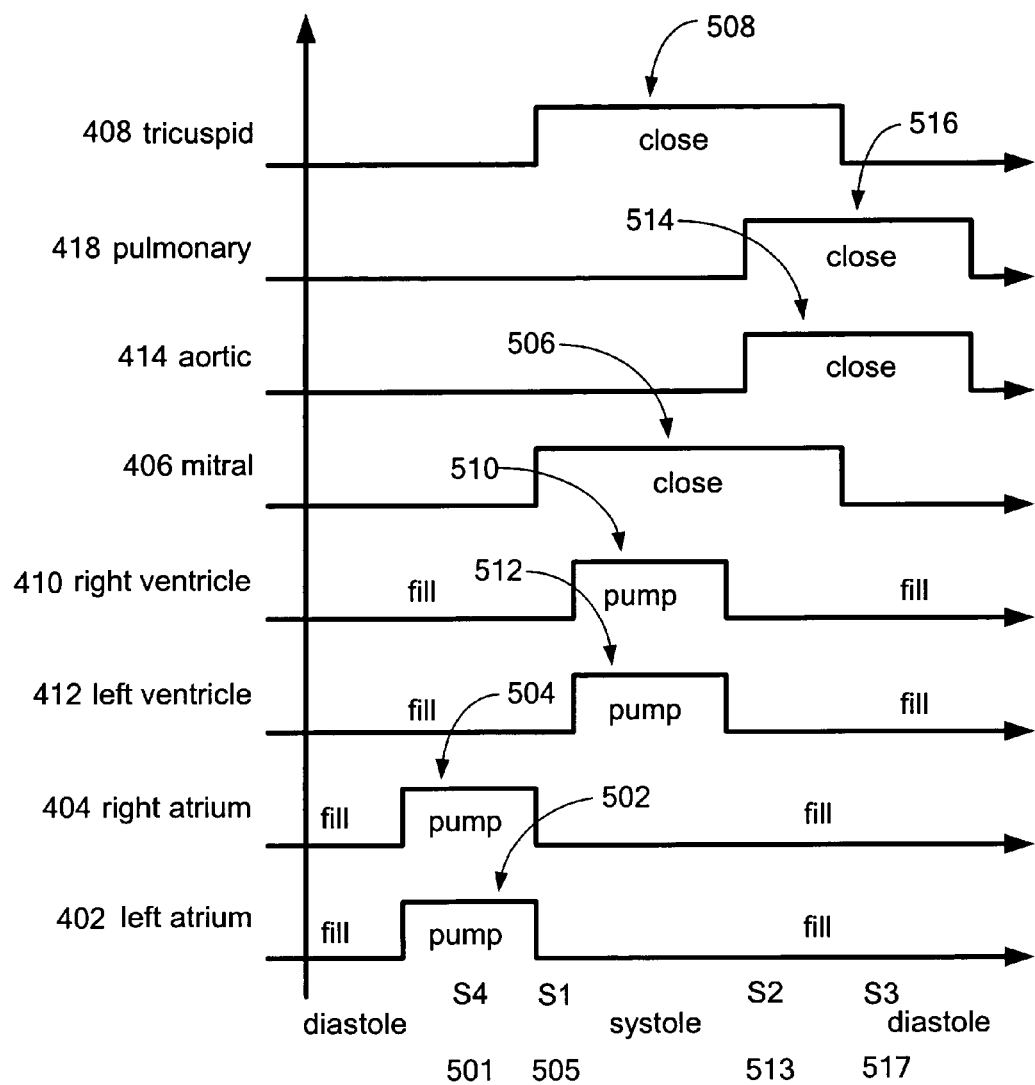
FIG. 5 is a representation of blood flow through the human heart of FIG. 4 that creates the heart sound information obtained by the sensor array.

FIG. 5 is a representation of blood flow through the human heart that creates the heart sound information 121 obtained by the sensor array 102. Prior to the onset of a cardiac cycle, the left atrium 402, the right atrium 404, the left ventricle 412, and the right ventricle 410 fill passively with blood. Then, the left atrium 402 and the right atrium 404 contract, 502 and 504, respectively and the right ventricle 410 and the left ventricle 412 fill actively with blood through the tricuspid valve 408 and the mitral valve 406 respectively, which creates a first low frequency sound ("S4") 501 during the end of diastole. The left atrium 402 and the right atrium 404 relax after contraction. Then, the left ventricle 412 and the right ventricle 410 begin to contract, 512 and 510, respectively, which causes the mitral valve 406, and the tricuspid valve 408 to close, 506 and 508, respectively. When the mitral valve 406 closes 506 and the tricuspid valve 408 closes 508, the mitral valve 406 and the tricuspid valve 408 create a first major sound ("S1") 505 of a heart sound of the heart sound information 121 during the beginning of systole.

During the next part of systole, the right ventricle 410 pumps blood 510 through the pulmonary valve 418 into the pulmonary artery 420, and the left ventricle 412 pumps blood 512 through the aortic valve 414 into the aorta 416. The right ventricle 410 and the left ventricle 412 relax upon completion of contraction at the end of systole, which causes the pulmonary valve 418 and the aortic valve 414 to close, 516 and 514, respectively. When the aortic valve 414 closes 514 and the pulmonary valve 418 closes 516, the aortic valve 414 and the pulmonary valve 418 create a second major sound ("S2") 513 of a heart sound of the heart sound information 121. Following, the second major sound, blood flow into one or more of the left atrium 402, the right atrium 404, the right ventricle 410, the left ventricle 412, the aorta 416, and the pulmonary artery 420 creates a second low frequency sound ("S3") 517 of the heart sound of the heart sound information during diastole.

Figure 6:
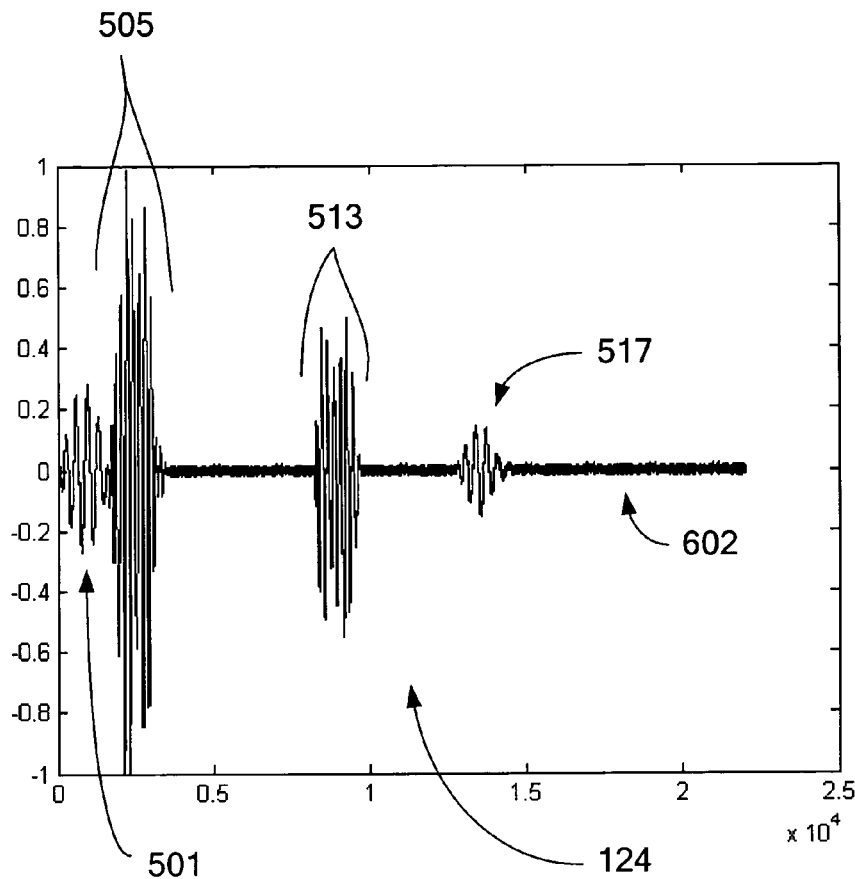
FIG. 6 is a representation of one exemplary plot of a composite heart sound of the heart sound information obtained through employment of the sensor array of the apparatus of FIG. 1.
Figure 7:
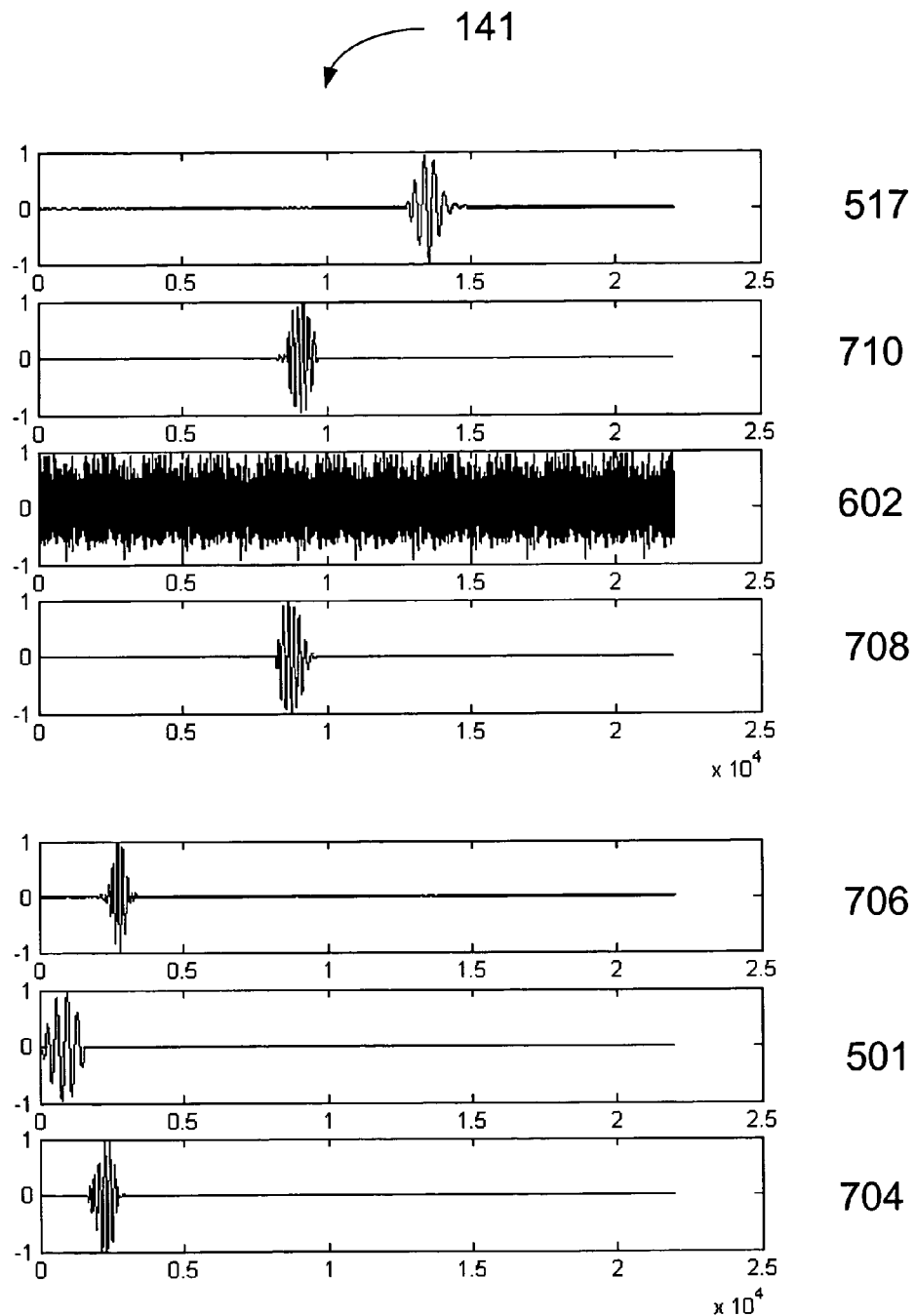
FIG. 7 is a representation of one exemplary plot of a plurality of discrete heart sounds extracted by the heart sound analyzer of FIG. 1 from the heart sound information.
Figure 8:
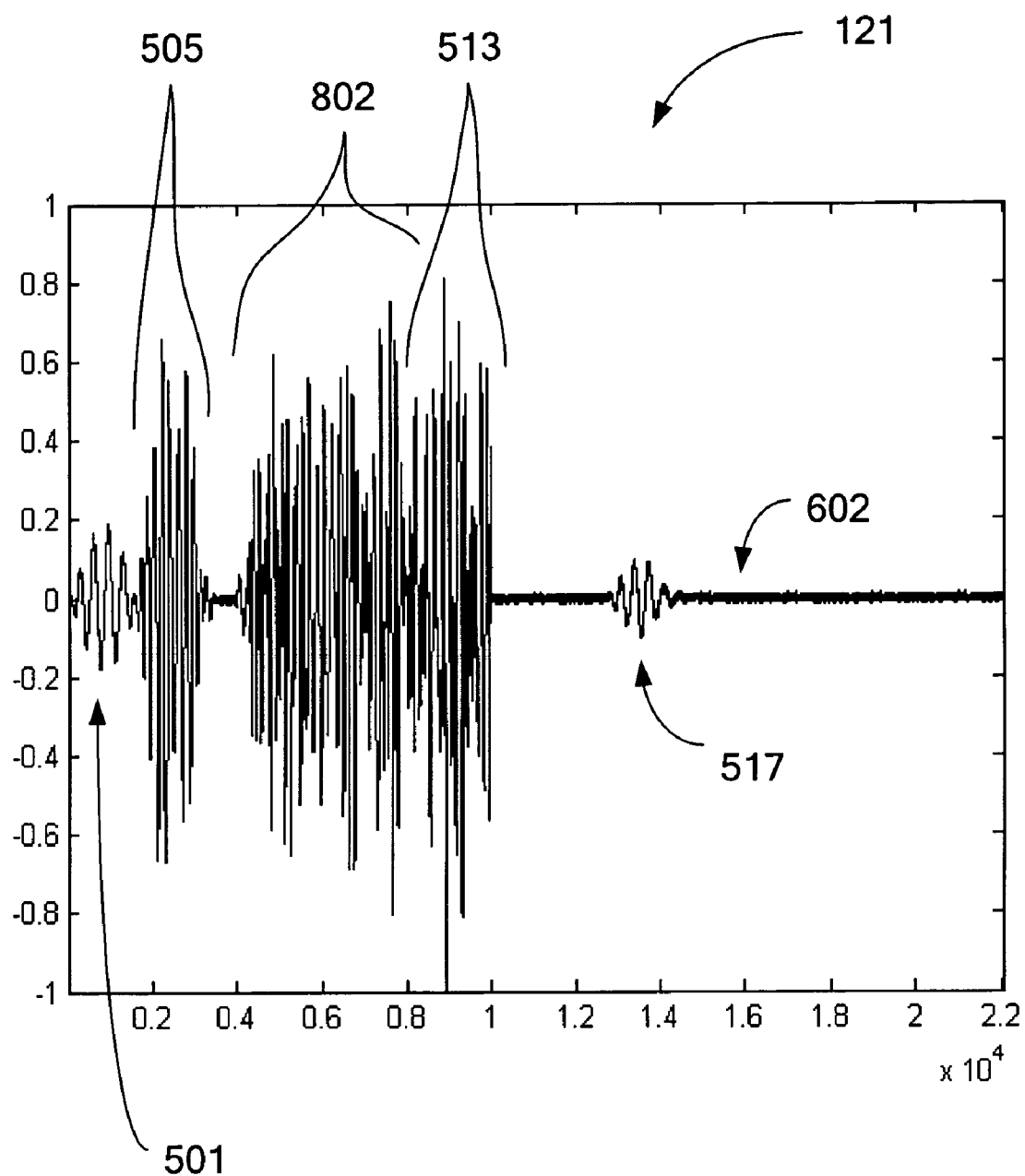
FIG. 8 is a representation of another exemplary plot of a composite heart sound of the heart sound information obtained through employment of the sensor array of the apparatus of FIG. 1.
Figure 9:
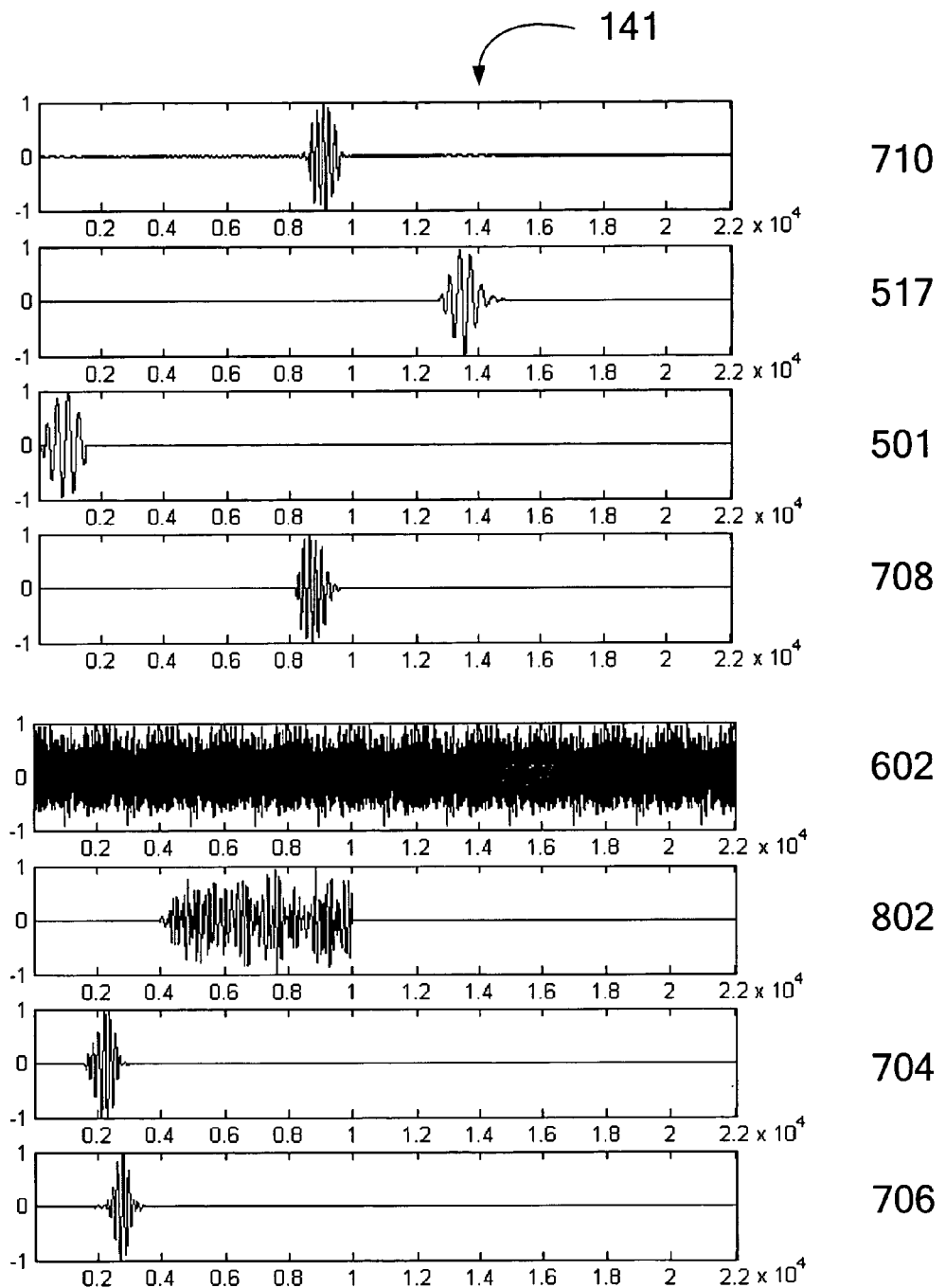
FIG. 9 is a representation of another exemplary plot of a plurality of discrete heart sounds extracted by the heart sound analyzer of FIG. 1 from heart sound information.

FIG. 6 is one exemplary plot of a composite heart sound from the heart sound information 121. The heart sound in one example comprises one or more of the first low frequency sound 501, the first major sound 505, the second major sound 513, the second low frequency sound 517, a noise sound component 602, and an abnormal sound 802 (FIGS. 8-9). The abnormal sound 802 in one example comprises a ventricular septal defect ("VSD").

A user 144 in one example places the sensor array 102 over the heart of the patient to obtain the heart sound information 121. The user 144 in one example comprises a doctor, an internist, a cardiologist, or a nurse. The sensor array 102 in one example comprises a plurality of the sensors 104, 106, 108, 110, 112, 114, 116, and 118. The plurality of sensors 104, 106, 108, 110, 112, 114, 116, and 118 comprise one or more microphones and/or acoustical sensors. The signal path 120 carries a voltage signal from the heart sound analyzer 140 to the sensors 104, 106, 108, 110, 112, 114, 116, and 118. For example, the voltage signal comprises a power supply for the plurality of sensors 104, 106, 108, 110, 112, 114, 116, and 118.

The plurality of sensors 104, 106, 108, 110, 112, 114, 116, and 118 in one example respectively connect to the signal paths 124, 126, 128, 130, 132, 134, 136, and 138. For example, the signal path 124 carries one composite heart sound of the plurality of composite heart sounds of the heart sound information 121 from the sensor 104 to the heart sound analyzer 140. The heart sound of the heart sound information 121 in one example comprises a composite heart sound obtained from the heart. The signal path 122 in one example carries a ground signal from the sensor array 102 to the heart sound analyzer 140. For example, the ground signal acts as a common reference signal for the sounds of the heart sound information 121 carried by the signal paths 124, 126, 128, 130, 132, 134, 136, and 138.

The heart sound analyzer 140 obtains the heart sound information 121 from the sensor array 102 through the signal paths 122, 124, 126, 128, 130, 132, 134, 136, and 138. In one example, the heart sound analyzer 140 is coupled to a computer. In another example, the heart sound analyzer 140 is an integral part of the computer dedicated to the analysis of the heart sound information 121. In still another example, the heart sound analyzer 140 is an integral part of the sensor array 102. The heart sound analyzer 140 comprises an instance of the recordable data storage medium 146. The heart sound analyzer 140 extracts from the heart sound information 121 a plurality of discrete heart sounds 141, for example, the discrete heart sounds of FIG. 7. The plurality of sensors 104, 106, 108, 110, 112, 114, 116, and 118 in one example comprise a plurality of sensors at least equal to the plurality of discrete heart sounds 141.

The plurality of discrete heart sounds 141 comprise one or more of the first low frequency sound 501, a mitral valve sound 704, a tricuspid valve sound 706, an aortic valve sound 708, a pulmonary valve sound 710, the second low frequency sound 517, the noise sound component 602, and the abnormal sound 802 (FIGS. 8-9). The first major sound 505 in one example comprises the mitral valve sound 704 and the tricuspid valve sound 706. The second major sound 513 in one example comprises the aortic valve sound 708 and the pulmonary valve sound 710. Where the plurality of discrete heart sounds 141 comprise the first low frequency sound 501, a mitral valve sound 704, a tricuspid valve sound 706, an aortic valve sound 708, a pulmonary valve sound 710, the second low frequency sound 517, the noise sound component 602, and the abnormal sound 802, the number of sensors comprises eight, for example, the plurality of sensors 104, 106, 108, 110, 112, 114, 116, and 118.

The heart sound analyzer 140 obtains the heart sound information 121 from the plurality of sensors 104, 106, 108, 110, 112, 114, 116, and 118. The speaker components 142 in one example obtain any one or more of the plurality of discrete heart sounds 141 from the heart sound analyzer 140. The speaker components 142 in one example comprise one or more of a mono speaker, a stereo speaker, a headphone, and a stethoscopic listening device. The user 144 in one example listens to the discrete heart sounds of the plurality of discrete heart sounds 141 with the speaker components 142 to diagnose one or more heart dysfunctions. For example, the user 144 hears the abnormal sound 802 with the speaker components 142 to diagnose the ventricular septal defect.

Figure 2:
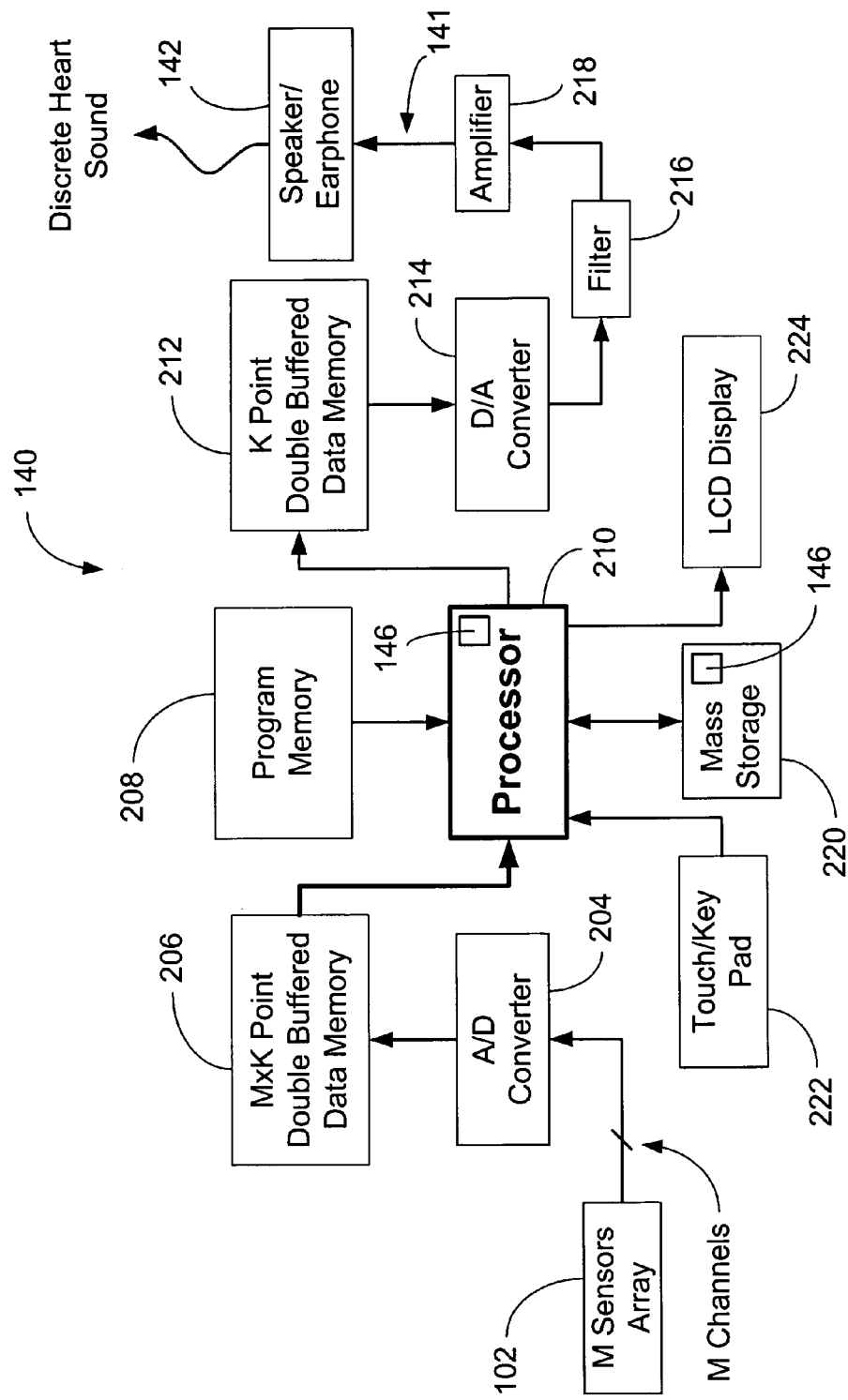
FIG. 2 is a representation of the heart sound analyzer of the apparatus of FIG. 1, and illustrates one or more analog to digital converters, one or more data buffer components, one or more software memory components, one or more processor components, one or more digital to analog converters, one or more filters, one or more amplifiers, one or more storage devices, one or more input devices, and one or more output devices.

Referring to FIGS. 1-2, the heart sound analyzer 140 comprises one or more analog to digital converters 204, one or more data buffer components 206 and 212, one or more software memory components 208, one or more processor components 210, one or more digital to analog converters 214, one or more filters 216, one or more amplifiers 218, one or more storage devices 220, one or more input devices 222, and one or more output devices 224. Upon receipt of the heart sound information 121 from the sensor array 102, the heart sound analyzer 140 processes the heart sound information 121 and outputs any one or more of the plurality of discrete heart sounds 141.

The analog to digital converter 204 in one example obtains the heart sound information 121 from the sensor array 102. The analog to digital converter 204 in one example digitizes the heart sound information 121. For example, the processor component 210 employs the analog-to-digital converter 204 to digitize the heart sound information 121. The analog-to-digital converter 204 in one example outputs an M×K matrix of data of the heart sound information 121 to the data buffer component 206, where, for example, M is the number of sensors in the sensor array 102 and K is the number of times the sensor array 102, i.e., the heart sound information 121, is sampled. The data buffer component 206 in one example comprises M×K point double buffered data memory.

Figure 10:
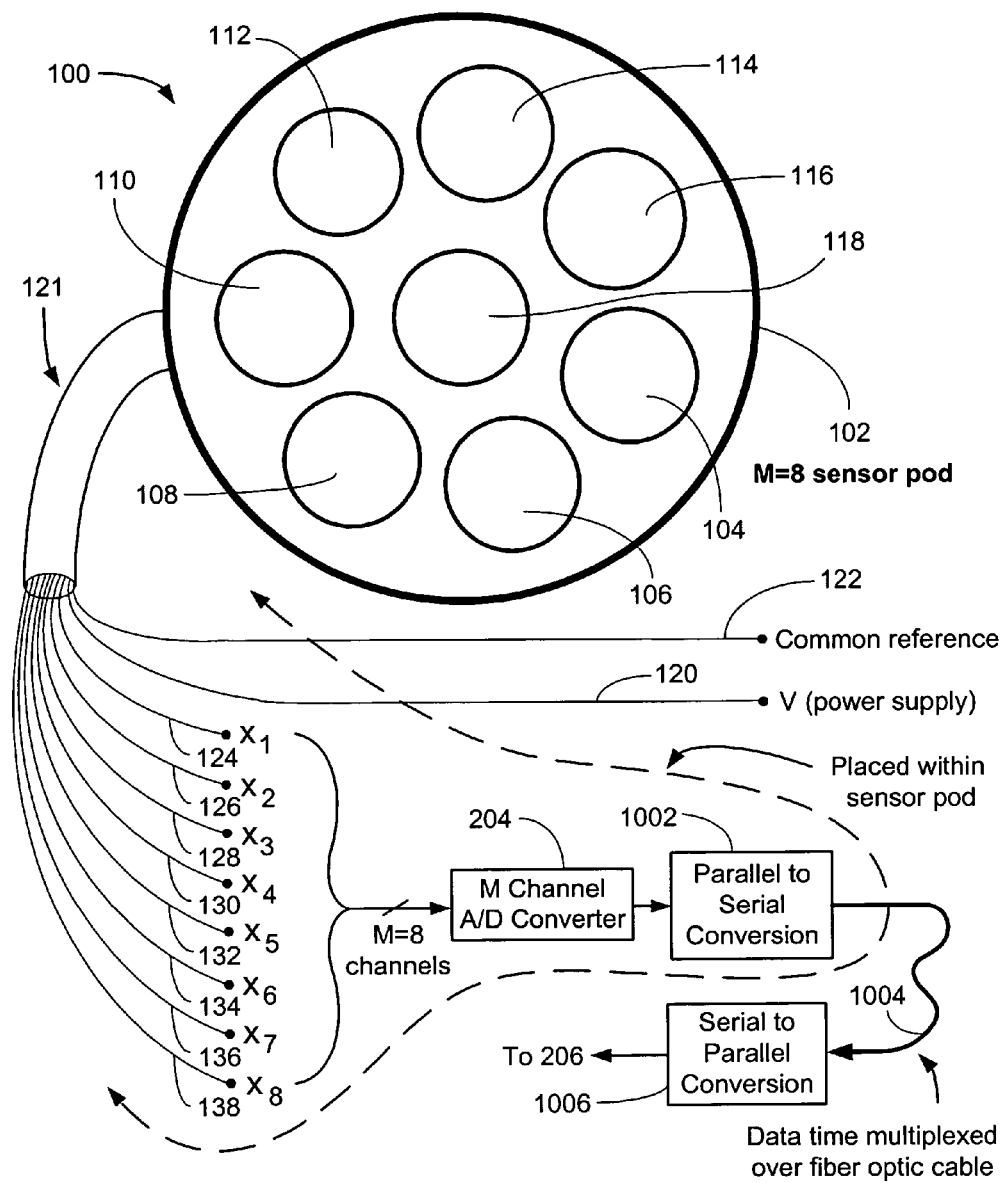
FIG. 10 is a representation of another exemplary implementation of the apparatus of FIG. 1 that comprises the sensor array and a serial to parallel converter, wherein the sensor array comprises the sensors, the signal paths, one or more analog to digital converters, and a parallel to serial converter.

Referring to FIGS. 1-2 and 10, the sensor array 102 in one example comprises the plurality of sensors 104, 106, 108, 110, 112, 114, 116, and 118, the signal paths 124, 126, 128, 130, 132, 134, 136, and 138, the analog to digital converter 204, and a parallel to serial converter 1002. For example, the analog to digital converter 204 and the parallel to serial converter 1002 are placed within a sensor pod. The analog to digital converter 204 digitizes the heart sound information 121 in parallel format to obtain one sample from each of the plurality of sensors 104, 106, 108, 110, 112, 114, 116, and 118. The parallel to serial converter 1002 obtains the heart sound information 121 in parallel format and outputs the heart sound information 121 in serial format. A serial cable 1004 carries the heart sound information 121 to a serial to parallel converter 1006. In one example, the serial cable 1004 comprises an electrical serial cable. The electrical serial cable is less affected by mechanical defects than the signal paths 124, 126, 128, 130, 132, 134, 136, and 138 because there is a single electrical cable versus eight signal paths. In another example, the serial cable 1004 comprises an optical serial cable. The optical serial cable is less affected by electrical/magnetic interference and/or mechanical defects than the signal paths 124, 126, 128, 130, 132, 134, 136, and 138. The serial to parallel converter 1006 obtains the heart sound information 121 in serial format from the serial cable 1004 and outputs the heart sound information 121 in parallel format to the data buffer component 206. The data buffer component 206 obtains the heart sound information 121 from the sensor array 102 through the analog to digital converter 204, the parallel to serial converter 1002, and the serial to parallel converter 1006 K times to fill an M×K matrix.

Figure 3:
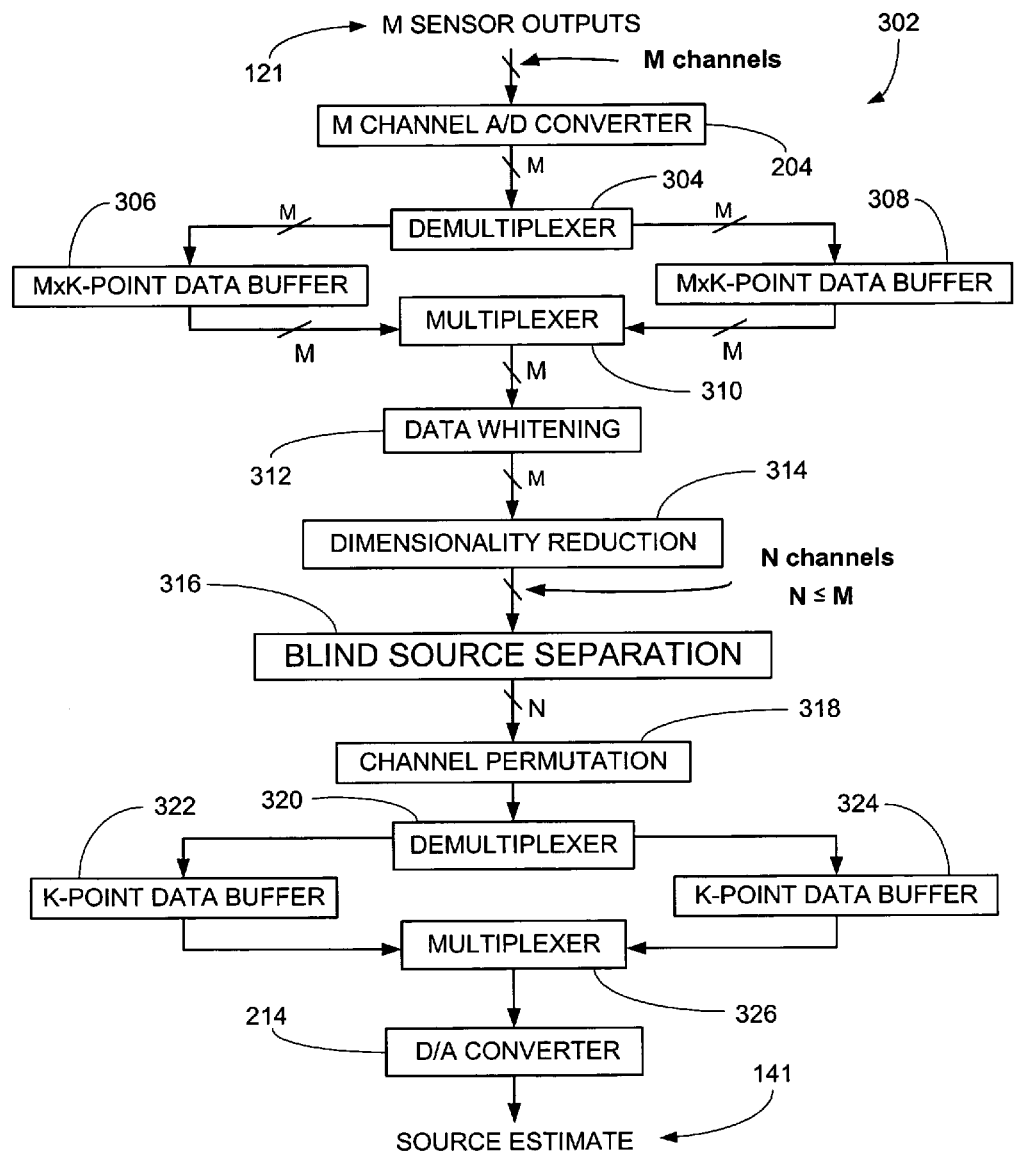
FIG. 3 is a representation of a functional block diagram that serves to allow the heart sound analyzer of the apparatus of FIG. 1 to extract from heart sound information one or more discrete heart sounds.

Referring to FIGS. 1-3, exemplary functional block diagram 302 serves to allow the processor component 210 of the heart sound analyzer 140 to extract from the heart sound information 121 the discrete heart sounds of the plurality of discrete heart sounds 141, as described herein. The apparatus 100 may employ independent component analysis to extract from the heart sound information 121 the discrete heart sounds of the plurality of discrete heart sounds 141. The functional block diagram 302 employs the analog to digital converter 204, the data buffer component 206, the data buffer component 212, and the digital to analog converter 214. The functional block diagram 302 also employs one or more steps, for example, STEPS 312, 314, 316, and 318.

The heart sound analyzer 140 in one example obtains the heart sound information 121 from the sensor array 102. The processor component 210 of the heart sound analyzer 140 in one example employs independent component analysis to extract from the heart sound information 121 the discrete heart sounds of the plurality of discrete heart sounds 141. In one example, the heart sound information 121 comprises a first discrete heart sound and a second discrete heart sound that occur contemporaneously. For example, the first discrete heart sound and the second discrete heart sound are mixed in the heart sound information 121. The heart sound analyzer 140 employs independent component analysis of the heart sound information 121 to create statistically independent outputs of one or more of the first discrete heart sound and the second discrete heart sound. One of the first and second discrete heart sounds may comprise an abnormal heart sound associated with a heart dysfunction. For example, the abnormal heart sound overlaps with one or more other sounds in the heart sound information 121. The heart sound analyzer 140 extracts the abnormal heart sound from the heart sound information 121. The user 144 in one example employs the speaker components 142 to listen to the abnormal heart sound for a diagnosis of the heart dysfunction.

The data buffer component 206 in one example provides the M×K matrix to the processor component 210. The data buffer component 206 in one example comprises the demultiplexer 304, the data buffers 306 and 308, and the multiplexer 310. The processor component 210 in one example controls the demultiplexer 304 to steer the output of the analog to digital converter 204 to fill the data buffer 306 with an M×K matrix. While the data buffer 306 is filling with data, the processor component 210 in one example controls the multiplexer 310 to steer data from the data buffer 308 to the processor component 210 until the processor component 210 has received an M×K matrix. The processor component 210 processes the M×K matrix with software stored in the software memory component 208.

After the processor 210 has completed processing the M×K matrix and the data buffer 306 has filled with data, the processor component 210 in one example controls the demultiplexer 304 to steer data to fill the data buffer 308 with an M×K matrix. While the data buffer 308 is filling with data, the processor component 210 in one example controls the multiplexer 310 to steer data from the data buffer 306 to the processor component 210 until the processor component 210 has received an M×K matrix. The processor component 210 again employs the software stored in the software memory component 208 to process the M×K matrix. By continuously reversing the roles of the data buffers 306 and 308, the heart sound analyzer 140 can work in real time.

The software memory component 208 in one example stores software for use by the processor component 210. The processor component 210 employs the software to extract from the heart sound information 121 the discrete heart sounds of the plurality of discrete heart sounds 141. The software memory component 208 in one example comprises an instance of the recordable data storage medium 146. The software memory component 208 in one example stores data whitening software, dimensionality reduction software, blind source separation software, and/or channel permutation software.

The data whitening software in one example reduces the noise sound component 602 of the heart sound information 121 to enhance the performance of the blind source separation software. For example, the processor component 210 transposes the M×K matrix and then forms an M×M correlation matrix, which is involved in whitening the K vectors of the M×K data matrix, and STEP 312 proceeds to STEP 314.

The processor component 210 in one example determines a plurality of eigen values of the M×M correlation matrix with the dimensionality reduction software. The processor component 210 reduces the plurality of eigen values so that the plurality of eigen values are equal in number to the plurality of discrete heart sounds 141, and STEP 314 proceeds to STEP 316.

Upon the dimensionality reduction, the processor component 210 employs blind source separation to extract from the heart sound information 121 the discrete heart sounds of the plurality of discrete heart sounds 141. For example, the processor component 210 employs independent component analysis in a neural network construct to extract from the heart sound information 121 the discrete heart sounds of the plurality of discrete heart sounds 141. The processor component 210 passes the heart sound information 121 through a plurality of neural network construct external nodes in number at least equal to the plurality of discrete heart sounds 141. At each external node of the plurality of external nodes, the processor component 210 passes the heart sound information 121 through a plurality of neural network construct internal nodes equal to the number of external nodes to determine one or more weights and zero or more delays of each of the plurality of discrete heart sounds 141. For example, the neural network construct outputs an N×K matrix that represents the discrete heart sounds of the plurality of discrete heart sounds 141, and STEP 316 proceeds to STEP 318. The discrete heart sounds of the plurality of discrete heart sounds 141 in one example are statistically independent.

Upon a formation of the N×K matrix, the processor component 210 in one example identifies a plurality of sources (e.g. one or more of the first low frequency sound 501, a mitral valve sound 704, a tricuspid valve sound 706, an aortic valve sound 708, a pulmonary valve sound 710, the first low frequency sound 501, the second low frequency sound 517, the noise sound component 602, and the abnormal sound 802) of the N×K matrix with the channel permutation software. For example, if a plurality of N curves represent the K vectors of the N×K matrix, the processor component 210 locates one or more peaks of each curve to identify the plurality of sources of the plurality of discrete heart sounds 141. The processor component 210 in one example comprises an instance of the recordable data storage medium 146.

After extraction of the plurality of discrete heart sounds 141 from the heart sound information 121, the processor component 210 stores the plurality of discrete of heart sounds 141. In one example, the processor component 210 stores the M×K matrix and/or the plurality of discrete heart sounds 141 in internal random access memory. In another example, the processor component 210 stores the M×K matrix and/or the plurality of discrete heart sounds 141 in the storage device 220. In yet another example, the processor component 210 may transfer the M×K matrix and/or the plurality of discrete heart sounds 141 from the heart sound analyzer 140 to another storage device through a wired or wireless connection.

The processor component 210 accesses one or any combination of one or more K vectors of the M×K matrix and the plurality of discrete heart sounds 141 with input from the user 144 of the heart sound analyzer 140. For example, the user 144 may employ the input devices 222 to cause the processor 210 to output one or more discrete heart sounds of the plurality of discrete heart sounds 141 (i.e. the N×K matrix) and/or the K vectors of the M×K matrix to one or more of the output devices 224 and the speaker components 142. The input devices 222 in one example comprise one or more of a button, a dial, a mouse, a keyboard, and a touch-screen. The output devices 224 in one example comprise a liquid crystal display ("LCD").

The user 144 in one example chooses with the input device 222 to listen to the one or any combination of the K vectors of the M×K matrix and the plurality of discrete heart sounds 141 with the speaker component 142. In another example, the user 144 chooses with the input device 222 to output one or more discrete heart sounds of the plurality of discrete heart sounds to the output devices 224. The user 144 may also choose to filter, amplify, and/or shift a spectral content of the one or any combination of the plurality of discrete heart sounds 141 from a first frequency range to a second frequency range with the processor component 210. In one example, the processor component 210 employs digital filtering software to filter out one or more frequency ranges of the one or any combination of the K vectors of the M×K matrix and the plurality of discrete heart sounds 141. In another example, the processor component 210 amplifies one or more regions of the one or any combination of the K vectors of the M×K matrix and the plurality of discrete heart sounds 141. In still another example, the processor component 210 may shift the spectral content of the one or any combination of the K vectors of the M×K matrix and the plurality of discrete heart sounds 141 for the user 144, where the user 144 hears better in the second frequency range than in the first frequency range.

The data buffer component 212 obtains data from the processor component 210. In one example, the data buffer component 212 obtains the one or any combination of the K vectors of the M×K matrix and the K vectors of the N×K matrix from the processor component 210. In another example, the data buffer component 212 obtains one or any combination of the discrete heart sounds of the plurality of discrete heart sounds 141. The data buffer component 212 in another example obtains one or any combination of the K vectors of the M×K matrix, the K vectors of the N×K matrix, and/or the discrete heart sounds of the plurality of discrete heart sounds 141, any one of which may have been spectrally modified, spectrally shifted, and/or amplified. The data buffer component 212 in one example comprises K point double buffered data memory.

Referring to FIGS. 2-3, the data buffer component 212 comprises the demultiplexer 320, the data buffers 322 and 324, and the multiplexer 326. The processor 210 in one example controls the demultiplexer 320 to steer data from the processor component 210 to fill the data buffer 322 with a K vector of data. While the data buffer 322 is filling with data, the processor component 210 in one example controls the multiplexer 326 to steer data from the data buffer 324 to the digital to analog converter 214 with a K vector of data. For example, the digital to analog converter 214 receives digital data points from the multiplexer 326 and outputs analog voltages based on the digital data points.

After the processor component 210 has output a K vector of data to the data buffer 322 and the digital to analog converter 214 has received a K vector of data from the data buffer 324, the processor component 210 in one example controls the demultiplexer 320 to steer data from the processor component 210 to fill the data buffer 324 with a K vector of data. While the data buffer 324 is filling with data, the processor component 210 in one example controls the multiplexer 326 to steer data from the data buffer 322 to the digital to analog converter 214 with a K vector of data. By continuously reversing the roles of the data buffers 322 and 324, the heart sound analyzer 140 can work in real time.

The digital to analog converter 214 in one example converts a digital representation of one or any combination of the K vectors of the M×K matrix, the K vectors of the N×K matrix, and the discrete heart sounds of the plurality of discrete heart sounds 141 into an analog representation of the one or any combination of the K vectors of the M×K matrix, the K vectors of the N×K matrix, and the discrete heart sounds of the plurality of discrete heart sounds 141. For example, the user can hear the one or any combination of the K vectors of the M×K matrix, the K vectors of the N×K matrix, and the discrete heart sounds of the plurality of discrete heart sounds 141 as a composite heart sound.

The digital to analog converter 214 in one example outputs the one or any combination of the K vectors of the M×K matrix, the K vectors of the N×K matrix, and the discrete heart sounds of the plurality of discrete heart sounds 141 to one or more of the speaker components 142, the filter 216, the amplifier 218, and the output devices 224. In one example, the filters 216 filter out one or more frequency ranges of the analog representation of the one or any combination of the K vectors of the M×K matrix, the K vectors of the N×K matrix, and the discrete heart sounds of the plurality of discrete heart sounds 141. The filters 216 in one example comprise one or more low pass filters. The amplifiers 218 in one example amplify an output of the filters 216 to drive the speaker components 142.

The user 144 employs one or more of the speaker components 142 and the output devices 224 to listen to and/or view the one or any combination of the K vectors of the M×K matrix, the K vectors of the N×K matrix, and the discrete heart sounds of the plurality of discrete heart sounds 141. Upon listening to or viewing the one or any combination of the K vectors of the M×K matrix, the K vectors of the N×K matrix, and the discrete heart sounds of the plurality of discrete heart sounds 141, the user 144 may diagnose one or more heart dysfunctions of the heart sound information 121. In still another example, the user 144 employs the heart sound analyzer 140 to automatically diagnose the heart dysfunctions. For example, the processor component 210 compares one or more features (e.g. signatures) of the one or any combination of the K vectors of the M×K matrix, K vectors of the N×K matrix, and the discrete heart sounds of the plurality of discrete heart sounds 141 to a normal range of the features (e.g. signatures) of the one or any combination of the K vectors of the M×K matrix, the K vectors of the N×K matrix, and the discrete heart sounds of the plurality of discrete heart sounds 141. If the one or any combination of the K vectors of the M×K matrix, the K vectors of the N×K matrix, and the discrete heart sounds of the plurality of discrete heart sounds 141 are outside of the normal range, then the one or any combination of the K vectors of the M×K matrix, the K vectors of the N×K matrix, and the discrete heart sounds of the plurality of discrete heart sounds 141 comprise one or more dysfunctions.

Figure 4:
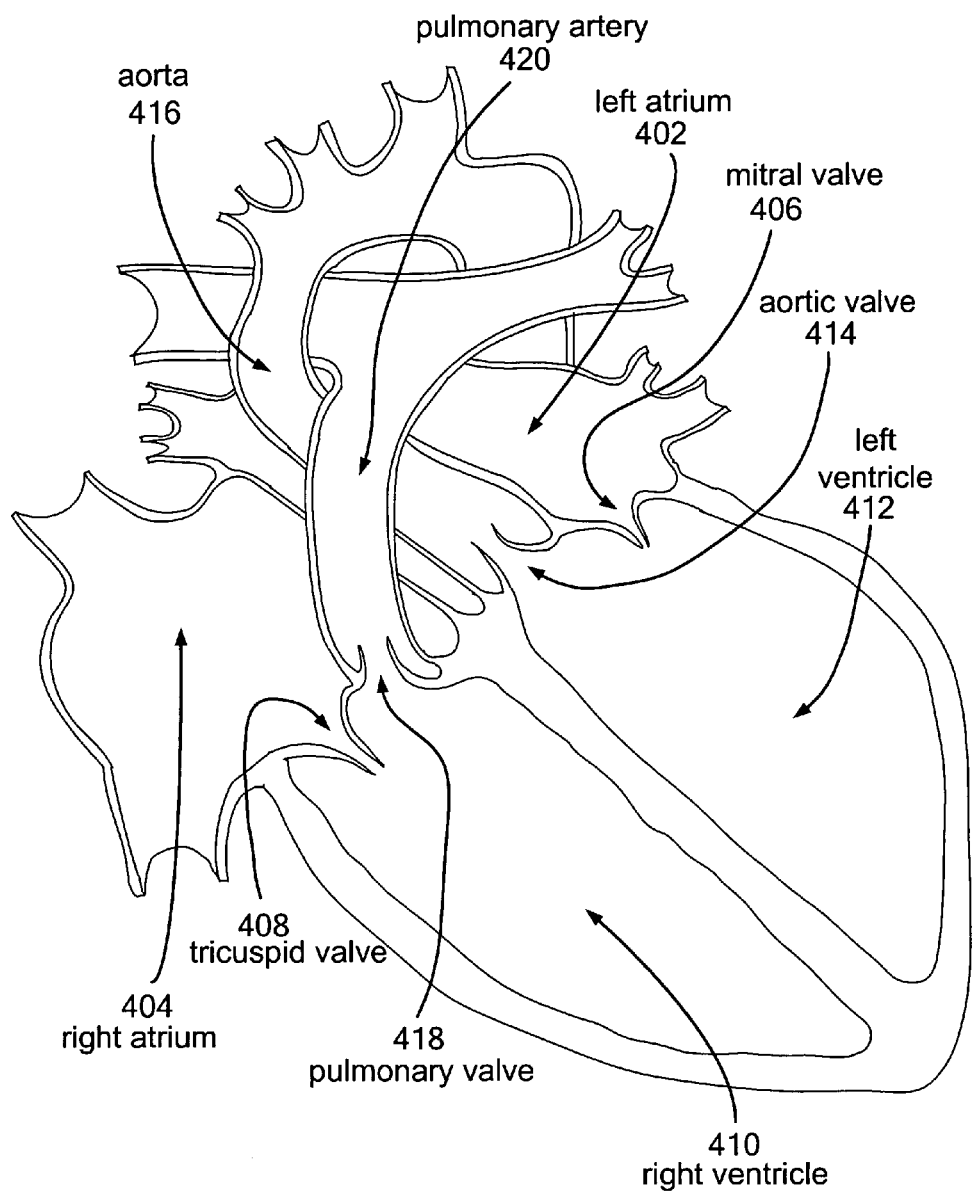
FIG. 4 is a representation of an exemplary human heart with which the sensor array of the apparatus of FIG. 1 is employable to obtain heart sound information.

Referring to FIGS. 1 and 4, the sensor array 102 in one example comprises a stethoscope sensor head that is locatable over a heart of a patient. The heart comprises a plurality of distinct heart sound sources, such as a sound from the mitral valve 406, a sound from the tricuspid valve 408, a sound from the aortic valve 414, a sound from the pulmonary valve 418, and the like. The stethoscope sensor head comprises a plurality of microphones (e.g., the plurality of sensors 104, 106, 108, 110, 112, 114, 116, and 118) in number at least equal to a number of the plurality of distinct heart sound sources. The plurality of microphones are sufficiently spaced to capture separate composite heart sounds.

In one example, the plurality of microphones are arranged on the stethoscope sensor head in a symmetrical geometry. In another example, the plurality of microphones are arranged on the stethoscope sensor head in a geometry compatible with a geometry of the plurality of distinct heart sound sources of the heart. For example, the heart comprises a plurality of heart valves, such as the mitral valve 406, the tricuspid valve 408, the aortic valve 414, and the pulmonary valve 418. The plurality of microphones are arranged on the stethoscope sensor head to be near the plurality of heart valves to capture strong audio signals from the plurality of heart valves. The plurality of microphones obtain and pass composite heart sound information to the heart sound analyzer 140.

Figure 11:
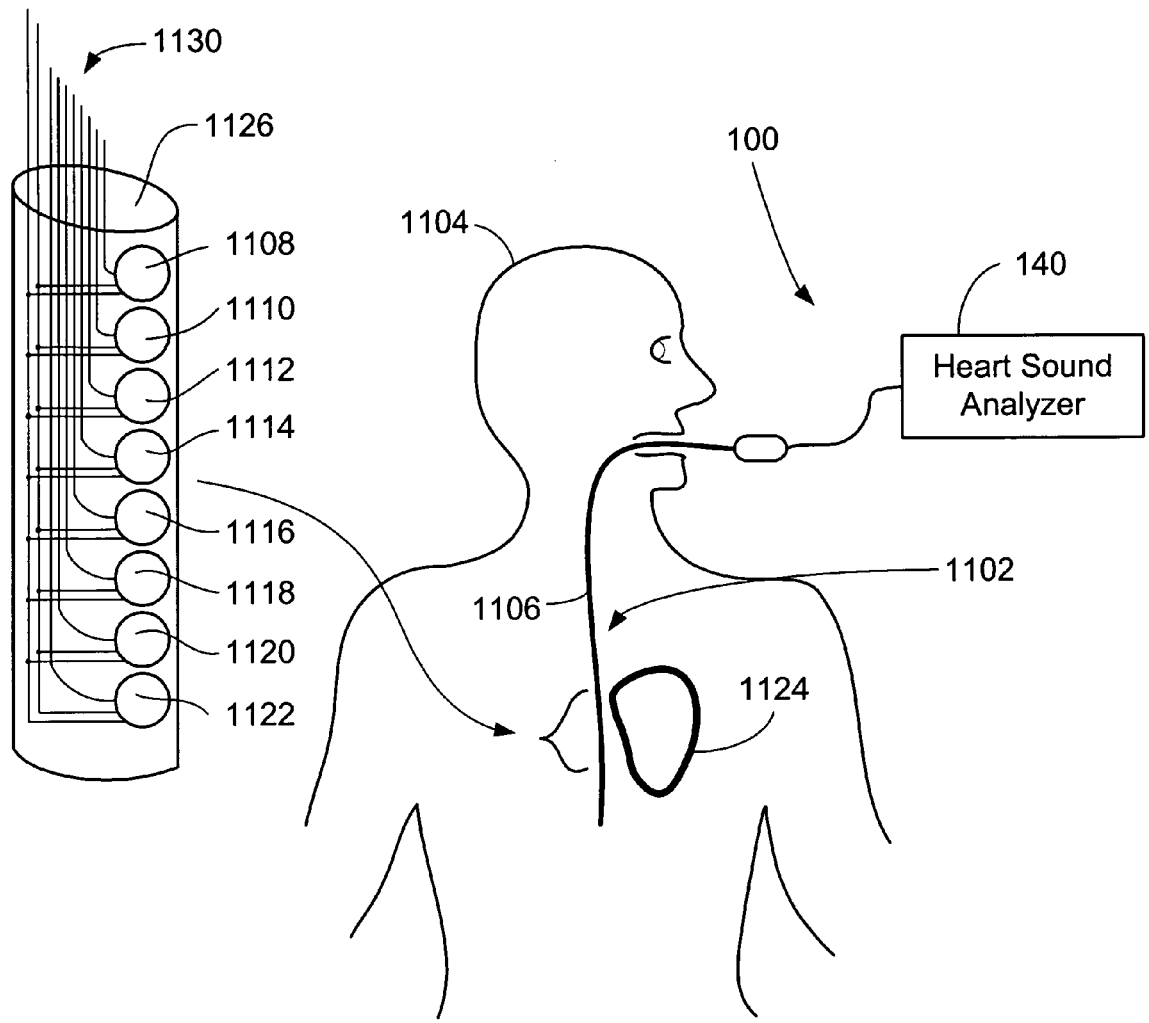
FIG. 11 is a representation of an embodiment of the sensor array of the apparatus of FIG. 1 that comprises an esophageal stethoscope sensor head that may pass down an esophagus of a patient.

Referring to FIG. 11, the sensor array 102 in one example comprises an esophageal stethoscope sensor head 1102 that may pass down an esophagus of a patient 1104. The esophageal stethoscope sensor head 1102 may pass down the esophagus of the patient 1104 so the plurality of microphones 1108, 1110, 1112, 1114, 1116, 1118, 1120, and 1122 are able to get closer to the heart 1124 of the patient 1104. For example, the esophageal stethoscope sensor head 1102 allows capture of heart sounds without distortion and/or volume reduction of the heart sounds that occurs from the heart sounds passing through the chest wall of the patient 1104.

The esophageal stethoscope sensor head 1102 comprises a flexible tube 1106 that contains a plurality of microphones 1108, 1110, 1112, 1114, 1116, 1118, 1120, and 1122 in number at least equal to a number of the plurality of distinct heart sound sources of the heart. The flexible tube 1106 in one example is filled with a gel to promote an increase in travel speed of sound through the flexible tube 1106. As illustrated in a magnified sectional view of a flexible tube portion 1126 of the flexible tube 1106, the plurality of microphones 1108, 1110, 1112, 1114, 1116, 1118, 1120, and 1122 are aligned in series along a length of the flexible tube 1106. In another example, the plurality of microphones 1108, 1110, 1112, 1114, 1116, 1118, 1120, and 1122 are arranged in the flexible tube 1106 in a geometry compatible with a geometry of the plurality of distinct heart sound sources of the heart.

A plurality of signal paths 1130 communicatively couple the plurality of microphones 1108, 1110, 1112, 1114, 1116, 1118, 1120, and 1122 with the heart sound analyzer 140. The plurality of signal paths 1130 also provide a power signal and a reference signal to the plurality of microphones 1108, 1110, 1112, 1114, 1116, 1118, 1120, and 1122. For example, the plurality of signal paths 1130 are analogous to the signal paths 120, 122, 124, 126, 128, 130, 132, 134, 136, and 138 (FIG. 1). The plurality of microphones 1108, 1110, 1112, 1114, 1116, 1118, 1120, and 1122 obtain and pass the composite heart sound information to the heart sound analyzer 140.

The apparatus 100 in one example comprises a plurality of components such as one or more of electronic components, hardware components, and computer software components. A number of such components can be combined or divided in the apparatus 100. An exemplary component of the apparatus 100 employs and/or comprises a set and/or series of computer instructions written in or implemented with any of a number of programming languages, as will be appreciated by those skilled in the art.

The apparatus 100 in one example employs one or more computer-readable signal-bearing media. Examples of a computer-readable signal-bearing medium for the apparatus 100 comprise the recordable data storage medium 146 of the heart sound analyzer 140, the program memory component 208, the processor component 210, and the storage device 220. For example, the computer-readable signal-bearing medium for the apparatus 100 comprises one or more of a magnetic, electrical, optical, biological, and atomic data storage medium. In one example, the computer-readable signal-bearing medium comprises a modulated carrier signal transmitted over a network comprising or coupled with the apparatus 100, for instance, one or more of a telephone network, a local area network ("LAN"), the internet, and a wireless network.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An apparatus, comprising:
a plurality of acoustic sensors that serve to obtain substantially simultaneously a plurality of heart sound signals, wherein the plurality of heart sound signals comprises a first heart sound signal S1 and a second heart sound signal S2, wherein the first heart sound signal S1 comprises a plurality of substantially contemporaneous acoustic signals produced by a first corresponding plurality of distinct heart structures of a living heart that comprises a mitral valve and a tricuspid valve; and
a processor that decomposes the first heart sound signal S1, acquired by the plurality of acoustic sensors, into one or more individual acoustic signals, that comprise an M1 sound of the mitral valve and a T1 sound of the tricuspid valve, of the plurality of substantially contemporaneous acoustic signals produced by the first corresponding plurality of distinct heart structures.

2. The apparatus of claim 1, wherein the processor employs independent component analysis to extract the one or more individual acoustic signals, that comprise the M1 sound of the mitral valve and the T1 sound of the tricuspid valve, of the plurality of substantially contemporaneous acoustic signals produced by the first corresponding plurality of distinct heart structures from the first heart sound signal S1.

3. The apparatus of claim 2,
wherein the processor implements the independent component analysis in a neural network construct that employs a plurality of nodes in number at least equal to a number of the first corresponding plurality of distinct heart structures to extract the one or more individual acoustic signals of the plurality of substantially contemporaneous acoustic signals produced by the first corresponding plurality of distinct heart structures from the first heart sound signal S1.

4. The apparatus of claim 1, wherein the one or more individual acoustic signals of the plurality of substantially contemporaneous acoustic signals produced by the first corresponding plurality of distinct heart structures comprise a first individual acoustic signal and a second individual acoustic signal;
wherein the first individual acoustic signal and the second individual acoustic signal occur substantially contemporaneously, wherein the first individual acoustic signal and the second individual acoustic signal are mixed in the first heart sound signal;
wherein the processor employs independent component analysis of the first heart sound signal S1 to create one or more statistically independent outputs that correspond to one or more of the one or more individual acoustic signals that comprise the M1 sound of the mitral valve and the T1 sound of the tricuspid valve of the plurality of substantially contemporaneous acoustic signals produced by the first corresponding plurality of distinct heart structures.

5. The apparatus of claim 1, further comprising:
a stethoscope sensor head that is locatable over the living heart;
wherein the stethoscope sensor head comprises a plurality of microphones in number at least equal to a number of the first corresponding plurality of distinct heart structures;
wherein the plurality of microphones obtains and passes the first heart sound signal S1 to the processor.

6. The apparatus of claim 1, further comprising:
an esophageal stethoscope sensor head that may pass down an esophagus of a patient that comprises the living heart;
wherein the esophageal stethoscope sensor head comprises a flexible tube that contains a plurality of microphones in number at least equal to a number of the first corresponding plurality of distinct heart structures;
wherein the plurality of microphones obtains and passes the first heart sound signal S1 to the processor.

7. The apparatus of claim 1, wherein a patient comprises the living heart, wherein the one or more individual acoustic signals of the plurality of substantially contemporaneous acoustic signals produced by the first corresponding plurality of distinct heart structures comprise an abnormal heart sound and one or more other sounds, wherein the abnormal heart sound overlaps with one or more of the one or more other sounds in the first heart sound signal S1;
wherein the abnormal heart sound is associated with a dysfunction of the living heart of the patient, wherein the processor extracts the abnormal heart sound from the first heart sound signal S1 and outputs the abnormal heart sound to a doctor for diagnosis of the dysfunction.

8. The apparatus of claim 1, wherein the processor decomposes the first heart sound signal S1 into a plurality of individual acoustic signals, that comprises the M1 sound of the mitral valve and the T1 sound of the tricuspid valve, of the substantially contemporaneous acoustic signals produced by the first corresponding plurality of distinct heart structures;
wherein the plurality of individual acoustic signals, that comprises the M1 sound of the mitral valve and the T1 sound of the tricuspid valve, of the substantially contemporaneous acoustic signals comprises the one or more individual acoustic signals that comprise the M1 sound of the mitral valve and the T1 sound of the tricuspid valve of the substantially contemporaneous acoustic signals.

9. The apparatus of claim 8, wherein the second heart sound signal S2 comprises a plurality of substantially contemporaneous acoustic signals produced by a second corresponding plurality of distinct heart structures of the living heart that comprises an aortic valve and a pulmonary valve;
wherein the processor decomposes the second heart sound signal S2 into a plurality of individual acoustic signals, that comprises an A2 sound of the aortic valve and a P2 sound of the pulmonary valve, of the substantially contemporaneous acoustic signals produced by the second corresponding plurality of distinct heart structures.

10. The apparatus of claim 8, wherein the first heart sound signal S1 is produced by nearly and/or approximately contemporaneous closures of the mitral valve and the tricuspid valve of the living hearts;
wherein the processor extracts from the first heart sound signal S1 the M1 sound as an individual acoustic signal of the closure of the mitral valve and T1 as an individual acoustic signal of the closure of the tricuspid valve;
wherein the plurality of individual acoustic signals comprises the M1 sound as the individual acoustic signal of the closure of the mitral valve and the T1 sound as the individual acoustic signal of the closure of the tricuspid valve.

11. The apparatus of claim 8, wherein the sound signal S2 is produced by nearly and/or approximately contemporaneous closures of an aortic valve and a pulmonary valve of the living heart;
wherein the processor extracts from decomposes the second heart sound signal S2 into an A2 sound as an individual acoustic signal of the closure of the aortic valve and a P2 sound as an individual acoustic signal of the closure of the pulmonary valve;
wherein the plurality of individual acoustic signals comprises the A2 sound as the individual acoustic signal of the closure of the aortic valve and the P2 sound as the individual acoustic signal of the closure of the pulmonary valve.

12. The apparatus of claim 1, wherein the processor decomposes the second heart sound signal S2 into a plurality of individual acoustic signals that comprises an A2 sound and a P2 sound produced by a second corresponding plurality of distinct heart structures of the living heart that comprises an aortic valve associated with the A2 sound and a pulmonary valve associated with the P2 sound.

13. The apparatus of claim 1, wherein the second heart sound signal S2 comprises a plurality of substantially contemporaneous acoustic signals produced by a second corresponding plurality of distinct heart structures of the living heart that comprises an aortic valve and a pulmonary valve;
wherein the processor decomposes the second heart sound signal S2 into one or more individual acoustic signals, that comprises an A2 sound of the aortic valve and a P2 sound of the pulmonary valve, of the substantially contemporaneous acoustic signals produced by the second corresponding plurality of distinct heart structures.

14. The apparatus of claim 1, wherein the processor in a time domain extracts from the first heart sound signal S1 the one or more individual acoustic signals, that comprise the M1 sound of the mitral valve and the T1 sound of the tricuspid valve, of the substantially contemporaneous acoustic signals produced by the first corresponding plurality of distinct heart structures.

15. The apparatus of claim 1, wherein a patient comprises the living heart, wherein the plurality of heart sound signals comprises one or more murmur signals, wherein the processor extracts the one or more of the murmur signals from plurality of heart sound signals and outputs the one or more of the murmur signals to a doctor for diagnosis of heart dysfunction of the living heart of the patient.

16. An apparatus, comprising:
a processor that extracts from a first heart sound signal one or more individual acoustic signals of a plurality of substantially contemporaneous acoustic signals produced by a first corresponding plurality of distinct heart structures of a living heart;

wherein the processor implements data whitening software on the first heart sound signal to facilitate blind source separation;

wherein after running the data whitening software, the processor employs dimensionality reduction software to determine one or more remaining eigen values of the first heart sound signal, wherein the processor decreases a total number of one or more eigen values until the one or more remaining eigen values are equal in number to a number of the one or more individual acoustic signals of the plurality of substantially contemporaneous acoustic signals produced by the first corresponding plurality of distinct heart structures;

wherein after running the dimensionality reduction software, the processor employs blind source separation software to extract the one or more individual acoustic signals of the plurality of substantially contemporaneous acoustic signals produced by the first corresponding plurality of distinct heart structures from the first heart sound signal.

17. The apparatus of claim 16, wherein after extraction of the one or more individual acoustic signals of the plurality of substantially contemporaneous acoustic signals produced by the first corresponding plurality of distinct heart structures from the first heart sound signal, the processor implements digital filtering software and/or channel permutation software to spectrally modify, spectrally shift, and/or amplify one or more of the one or more individual acoustic signals of the plurality of substantially contemporaneous acoustic signals produced by the first corresponding plurality of distinct heart structures.

18. The apparatus of claim 17, wherein the processor implements the digital filtering software and/or the channel permutation software to identify the first corresponding plurality of distinct heart structures associated with the one or more individual acoustic signals of the plurality of substantially contemporaneous acoustic signals produced by the first corresponding plurality of distinct heart structures.

19. A method, comprising the steps of:

obtaining substantially simultaneously a plurality of heart sound signals through employment of a plurality of acoustic sensors, wherein the plurality of heart sound signals comprises a first heart sound signal S1 and a second heart sound S2, wherein the first heart sound signal S1 comprises a plurality of substantially contemporaneous acoustic signals produced by a first corresponding plurality of distinct heart structures of a living heart that comprises a mitral valve and a tricuspid valve; and decomposing the first heart sound signal S1, acquired by the plurality of acoustic sensors, into one or more individual acoustic signals, that comprise an M1 sound of the mitral valve and a T1 sound of the tricuspid valve, of the plurality of substantially contemporaneous acoustic signals produced by the first corresponding plurality of distinct heart structures.

* * * * *

UNITED STATES PATENT AND TRADEMARK OFFICE
CERTIFICATE OF CORRECTION

| | |
|---|---|
| PATENT NO. | : 7,351,207 B2 |
| APPLICATION NO. | : 10/893627 |
| DATED | : April 1, 2008 |
| INVENTOR(S) | : Roland Priemer |

Page 1 of 1

It is certified that error appears in the above-identified patent and that said Letters Patent is hereby corrected as shown below:

In column 14, line 15 claim 11, after the second instance of "the", insert --second heart--;
In column 14, line 19 claim 11, delete "extracts from".

Signed and Sealed this

Twelfth Day of August, 2008

JON W. DUDAS
*Director of the United States Patent and Trademark Office*